US012357763B2

United States Patent
Dahmen et al.

(10) Patent No.: US 12,357,763 B2
(45) Date of Patent: Jul. 15, 2025

(54) INJECTION DEVICE (71) Applicant: Sanofi-Aventis Deutschland GMBH, Frankfurt am Main (DE)

(72) Inventors: Michael Dahmen, Kronberg (DE); Hannes Obex, Dusseldorf (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1062 days.

(21) Appl. No.: 17/269,646

(22) PCT Filed: Aug. 27, 2019

(86) PCT No.: PCT/EP2019/072759
§ 371 (c)(1),
(2) Date: Feb. 19, 2021

(87) PCT Pub. No.: WO2020/043685
PCT Pub. Date: Mar. 5, 2020

(65) Prior Publication Data
US 2021/0361876 A1 Nov. 25, 2021

(30) Foreign Application Priority Data

Aug. 29, 2018 (EP) .................................... 18191424

(51) Int. Cl.
*A61M 5/315* (2006.01)
*A61M 5/24* (2006.01)

(52) U.S. Cl.
CPC .......... *A61M 5/31543* (2013.01); *A61M 5/24* (2013.01); *A61M 5/31501* (2013.01);
(Continued)

(58) Field of Classification Search
CPC ................ A61M 5/31543; A61M 5/24; A61M 5/31501; A61M 5/31551;
(Continued)

(56) References Cited

U.S. PATENT DOCUMENTS

2011/0319835 A1\* 12/2011 Burren .............. A61M 5/31551
604/209
2014/0074042 A1\* 3/2014 Schneider ......... A61M 5/31543
604/220
(Continued)

FOREIGN PATENT DOCUMENTS

| CN | 103313743 | 9/2013 |
| CN | 106794312 | 5/2017 |

(Continued)

OTHER PUBLICATIONS

Translation of WO 2012/069085 (Year: 2012).\*
(Continued)

*Primary Examiner* — Dung T Ulsh
(74) *Attorney, Agent, or Firm* — Bond, Schoeneck & King, PLLC (57) ABSTRACT

The present disclosure refers to an injection device comprising a housing, a cartridge holder having a first attachment member, a threaded sleeve insert axially and rotationally constrained to the housing, the threaded sleeve insert having a second attachment member for releasable attachment with the first attachment member, and a metering mechanism. The metering mechanism comprises an actuating element, a piston rod, a piston rod sleeve in which the piston rod can be non-rotatably connected in the piston rod sleeve, and a coupling element coupling the actuating element and the piston rod sleeve. The piston rod can be non-rotatably connected to the piston rod sleeve by a coupling sleeve. The cartridge holder is attached to the threaded sleeve insert by axially moving cartridge holder with respect to the threaded sleeve insert and the housing to engage the coupling sleeve with the piston rod sleeve.

27 Claims, 2 Drawing Sheets

(52) U.S. Cl.
CPC .................. *A61M 5/31551* (2013.01); *A61M 2005/2477* (2013.01); *A61M 2005/2485* (2013.01); *A61M 2005/3154* (2013.01)

(58) Field of Classification Search
CPC ............ A61M 2005/2477; A61M 2005/2485; A61M 2005/3154
See application file for complete search history.

(56) References Cited

U.S. PATENT DOCUMENTS

| | | | |
|---|---|---|---|
| 2016/0129196 A1 | 5/2016 | Hirschel et al. | |
| 2017/0348489 A1* | 12/2017 | Hirschel | A61M 5/24 |
| 2020/0282147 A1* | 9/2020 | Quinn | A61M 5/31575 |

FOREIGN PATENT DOCUMENTS

| | | | |
|---|---|---|---|
| EP | 2643036 | 11/2017 | |
| JP | 2011-519599 | 7/2011 | |
| WO | WO 2009/132777 | 11/2009 | |
| WO | WO 2012/069085 | 5/2012 | |
| WO | WO-2012069085 A1 * | 5/2012 | ........ A61M 5/31525 |
| WO | WO 2016/055631 | 4/2016 | |

OTHER PUBLICATIONS

PCT International Preliminary Report on Patentability in International Application No. PCT/EP2019/072759, dated Mar. 2, 2021, 9 pages.

PCT International Search Report and Written Opinion in International Application No. PCT/EP2019/072759, dated Oct. 1, 2019, 11 pages.

* cited by examiner

INJECTION DEVICE

CROSS-REFERENCE TO RELATED APPLICATIONS

The present application is the national stage entry of International Patent Application No. PCT/EP2019/072759, filed on Aug. 27, 2019, and claims priority to Application No. EP 18191424.3, filed on Aug. 29, 2018, the disclosures of which are incorporated herein by reference.

TECHNICAL FIELD

The present disclosure is generally directed to a drug delivery device, e.g. an injection device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is further directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

EP 2 643 036 B1 discloses a resettable injection device comprising a coupling sleeve guiding a piston rod, wherein the coupling sleeve can be coupled to and de-coupled from a piston rod sleeve which drives the piston rod during dose discharging when coupled to the coupling sleeve. For resetting of the device, the coupling sleeve is de-coupled from the piston rod sleeve. This coupling and de-coupling is caused by attachment and detachment of a cartridge holder to a housing of the device in combination with an interaction of several component parts. This operation is complex because a rotation without axial movement of the cartridge holder is translated into an axial movement of the coupling sleeve.

SUMMARY

Certain aspects of the present disclosure provide an improved injection device which allows a simplified resetting of the piston rod.

An injection device preferably comprises a housing having a central axis, a distal end and a proximal end, a cartridge holder for receiving a cartridge containing a medicament, the cartridge holder having a first attachment member, a threaded sleeve insert axially and rotationally constrained to the housing, the threaded sleeve insert having a second attachment member for releasable attachment of the cartridge holder by means of interaction with the first attachment member, and a metering mechanism. The metering mechanism may comprise an actuating element for setting or discharging a dose from the injection device, a piston rod for producing an advance movement for dispensing a dose, a piston rod sleeve in which the piston rod is accommodated such that the piston rod can be non-rotatably connected to the piston rod sleeve, a coupling element with which the actuating element and the piston rod sleeve can be coupled for discharge of the dose set with the actuating element in such a way that a dispensing movement of the actuating element is transmitted to the piston rod by way of the piston rod sleeve connected to the piston rod. The metering mechanism may further comprise a reverse rotation prevention element for the piston rod sleeve, to permit rotation of the piston rod sleeve in one direction and to block it in the opposite direction. In addition the piston rod can be non-rotatably connected to the piston rod sleeve by means of a coupling sleeve wherein the coupling sleeve can be in engagement with the piston rod sleeve to form a non-rotatable connection between the piston rod and the coupling sleeve and wherein the coupling sleeve can be out of engagement with the piston rod sleeve such that the piston rod is rotatable relative to the piston rod sleeve.

The present disclosure is based on the idea that the number of component parts required for coupling and de-coupling of the coupling sleeve and the complexity of this operation may be reduced by using an axial movement of the cartridge holder for coupling and de-coupling of the coupling sleeve. Resetting of an injection device is typically required when an empty cartridge is replaced by a new cartridge. Replacement of the cartridge requires detachment of the cartridge holder from the housing or the like of the injection device followed by reattachment of the cartridge holder which typically involves an axial movement of the cartridge holder with respect to the housing or the like. For example, the cartridge holder may perform a combined axial and rotational movement for attachment and detachment and/or may perform an axial movement followed by a rotational movement or vice versa.

In an embodiment of the present disclosure, attachment of the cartridge holder to the threaded sleeve insert by means of interaction of the first attachment member and the second attachment member includes an axial movement of the cartridge holder with respect to the threaded sleeve insert and the housing. Preferably, this axial movement brings the coupling sleeve in engagement with the piston rod sleeve. In a similar manner, detachment of the cartridge holder from the threaded sleeve insert includes an axial movement of the cartridge holder in the opposite direction, thereby causing and/or permitting disengagement of the coupling sleeve from the piston rod sleeve.

In another embodiment of the present disclosure, the cartridge holder comprises at least one axially extending protrusion, e.g. directly, abutting the coupling sleeve during this axial movement for attachment of the cartridge holder to the threaded sleeve insert, such that a common axial movement of the cartridge holder and the coupling sleeve brings the coupling sleeve in engagement with the piston rod sleeve. In this embodiment the cartridge holder pushes the coupling sleeve from its de-coupled state into its coupled state engaging the piston rod sleeve. This embodiment has the benefit of requiring significantly less component parts compared with the prior art example known from EP 2 643 036 B1 because translating a rotational movement of the cartridge holder into an axial movement of the coupling sleeve may be omitted. Especially for injection devices which are mass-produced reducing the number of component parts contributes to lower production costs and less assembly effort.

According to an alternative embodiment, the injection device further comprises a coupling ring axially constrained to the coupling sleeve. In this embodiment the cartridge holder may comprise a contact face, e.g. directly, abutting the coupling ring during this axial movement for attachment of the cartridge holder to the threaded sleeve insert, such that a common axial movement of the cartridge holder, the coupling ring and the coupling sleeve brings the coupling sleeve in engagement with the piston rod sleeve. Interposing the coupling ring between the coupling sleeve and the cartridge holder may have benefits in guiding the coupling sleeve in the injection device. For example, the coupling ring may be axially guided in the threaded sleeve insert and rotatable with respect to the threaded sleeve insert. In other words, the axial movement of the cartridge holder is transmitted onto the coupling ring which in turn moves the coupling sleeve.

While transmitting axial movement of the cartridge holder directly or indirectly to the coupling sleeve pushes the coupling sleeve into a position engaging the piston rod sleeve in a reliable manner, disengaging the coupling sleeve from the piston rod sleeve by pulling the coupling sleeve from the piston rod sleeve due to the axial movement of the cartridge holder may be more complex. According to an embodiment of the disclosure, the injection device further comprises a clutch spring. The clutch spring may exert a force on the coupling sleeve (either directly or indirectly via one or more interposed component parts) to bring the coupling sleeve out of engagement with the piston rod sleeve when the cartridge holder is detached from the threaded sleeve insert. In other words, the coupling sleeve may be held in engagement with the piston rod sleeve by means of the position of the cartridge holder against the biasing force of the clutch spring such that the clutch spring disengages the coupling sleeve from the piston rod sleeve as soon as the cartridge holder is removed from its position attached to the injection device. For example, the clutch spring, e.g. a compression spring, may be interposed between the coupling sleeve and the piston rod sleeve.

Attachment and detachment of the cartridge holder with respect to the injection device or a housing component or insert thereof may comprise at least a portion of a pure axial movement of the cartridge holder relative to the housing component or insert. This pure axial movement may follow or a may be followed by a pure rotational movement or a combined axial and rotational movement, for example as in a bayonet attachment. As an alternative, the cartridge holder may perform a combined axial and rotational movement with respect to the housing component or insert, for example as in the threaded attachment. For example, the first attachment member and the second attachment member comprise a cam and a guide track, wherein the guide track comprises at least one portion guiding the cartridge holder with the cam at least partially axially or on a helical path with respect to the threaded sleeve insert.

The actuating element may be coupled to the coupling element such that an axial movement of the actuating element for setting a dose is transmitted to the coupling element. For example, the coupling element may be entrained by the actuating element during dose setting. In addition or as an alternative, the actuating element may be coupled to the coupling elements such that the rotational movement of the actuating element for discharging a dose, e.g. a movement along a helical path, is transmitted to the coupling element. Further, the coupling element may have a coupling member and the actuating element may have a counterpart coupling member which can be coupled or opened relative to each other by an axial or radial displacement of the coupling element relative to the actuating element. For example, the actuating element may comprise a shoulder as the counterpart coupling member and the coupling element may comprise a flange as the coupling member arranged such that an axial movement of the actuating element for setting a dose is transmitted to the coupling element. The coupling member and the counterpart coupling member may each be provided with teeth adapted to engage and disengage for coupling and decoupling, respectively.

According to a further aspect of the present disclosure, the coupling element and the piston rod sleeve may comprise splines or the like preventing relative rotation of the coupling element and the piston rod sleeve and permitting relative axial displacement of the coupling element and the piston rod sleeve.

The reverse rotation prevention element of the metering mechanism and the piston rod sleeve may be in engagement by means of a tooth means or a latching means. For example, the reverse rotation prevention element has a spring arm or is in the form of a spring arm. Further, the reverse rotation prevention element and the piston rod sleeve may be coupled to each other. The reverse rotation prevention element is e.g. non-rotatably and axially fixedly connected to a housing of the metering mechanism.

The injection device typically comprises a cartridge containing a medicament. The term "medicament", as used herein, means a pharmaceutical formulation containing at least one pharmaceutically active compound.

wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Non-limiting, exemplary embodiments of the invention will now be described with reference to the accompanying drawings, in which.

BRIEF DESCRIPTION OF THE FIGURES

DETAILED DESCRIPTION

Figure 1:
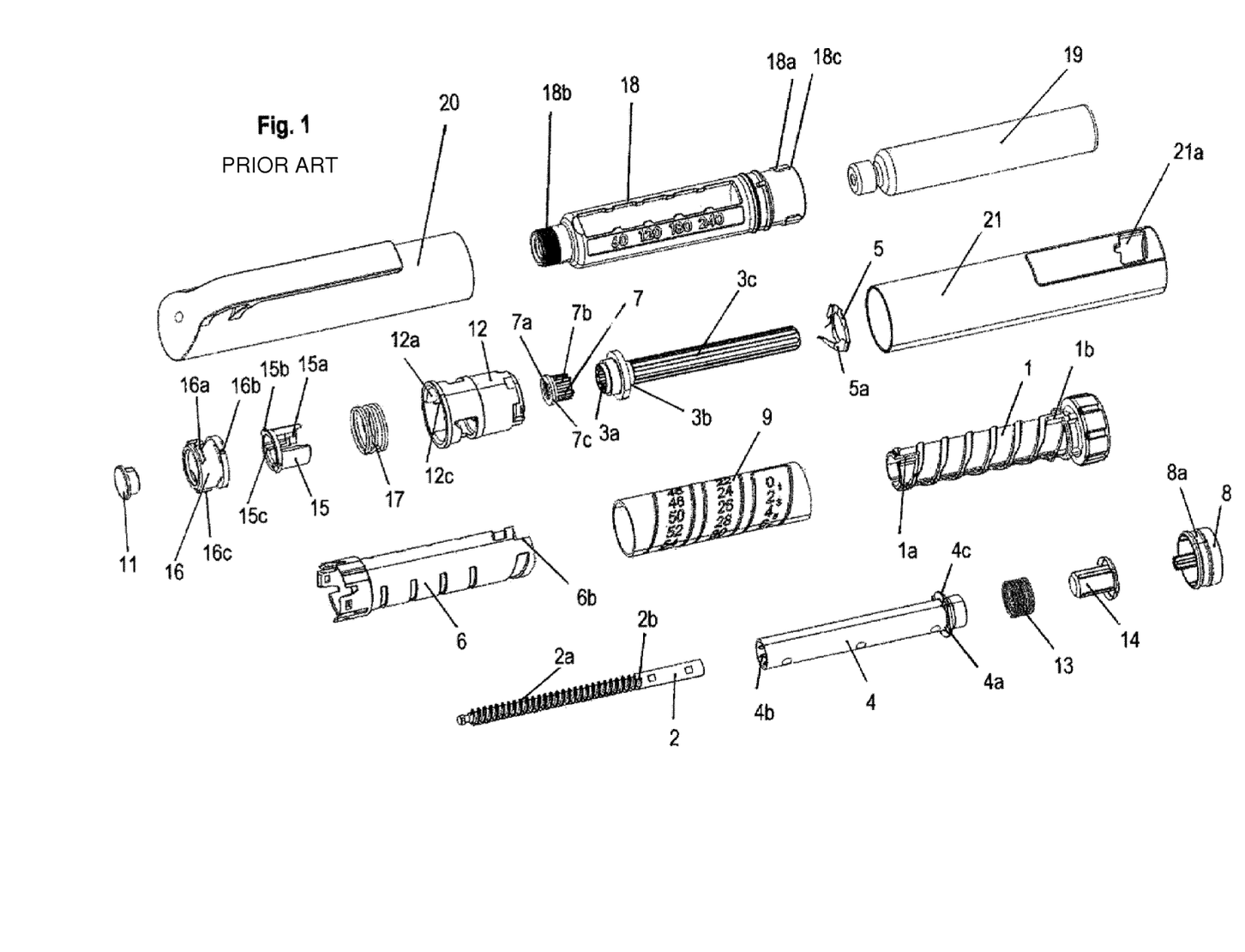
FIG. 1 schematically shows an injection device according to the prior art.

Referring to FIG. 1, there is shown an injection device as disclosed in EP 2 643 036 B1 with a metering mechanism. The metering mechanism comprises an actuating element 1 for setting and delivering a dose. The actuating element 1 has an external thread 1b, which is guided into an internal thread of an internal housing 6 of the metering mechanism. To set a dose, the actuating element 1 is screwed out of the housing 6 while the actuating element 1 is screwed back into the housing 6 to deliver (discharge) a dose. A number sleeve 9 (display sleeve) is arranged axially and rotationally fixed on the actuating element 1, to display the actually set dose in a display window 21a of an outer housing sleeve 21 which coaxially surrounds the housing 6. At a distal end of the external thread 1b, there is a stop cam 1a cooperating with a corresponding counter cam (not shown) of the housing 6 to limit the setting of a maximum dose. In stop contact, the actuating element 1 cannot be unscrewed further out of the housing 6. A further stop cam 6b is provided as a minimum dose stop, typically preventing setting a dose below the dose value zero.

In the metering mechanism, a piston rod 2 is movably mounted with an external thread 2a for generating a movement for dispensing a dose. At the distal end of the piston rod 2, a pressure foot or flange 11 is rotatably arranged. During the advancing movement of the piston rod 2, the flange 11 abuts a rubber bung, which is movably received in a cartridge 19 in order to deliver a medicament from the injection device. The cartridge 19 is received in a cartridge holder 18. A detachable protective cap 20 is provided for receiving the cartridge holder 18.

The external thread 2a of the piston rod 2 is in a threaded engagement with an internal thread of a threaded sleeve insert 12 (also referred to as threaded sleeve in the following description). The threaded sleeve 12 is axially and rotatably constrained to the housing 6 via the outer housing sleeve 21. The threaded sleeve 12 serves to transform a rotational movement of the piston rod 2 in a combined rotational and axial movement of the piston rod 2. A stop cam 2b of the piston rod 2 can come into abutment contact with the threaded sleeve 12 when the cartridge 19 is empty. The distal end of the cartridge holder 18 has a thread 18b to connect a needle unit to the cartridge 19. At the proximal end of the cartridge holder 18 there is an outwardly projecting locking cam 18a which can be brought into engagement with a guide 12a in the threaded sleeve 12 to form a bayonet locking.

A piston rod sleeve 3 surrounds the piston rod 2 coaxially. A coupling sleeve 7 is provided for coupling the piston rod 2 detachably with the piston rod sleeve 3. For this purpose, the coupling sleeve 7 is rotationally constrained to the piston rod 2, for example by means of a rib 7a provided on an inner surface of the coupling sleeve 7 engaging a longitudinally extending groove of the piston rod 2. Further, longitudinally extending ribs 7b are arranged on an outer surface of the coupling sleeve 7 which engage grooves 3a on an inner surface of the piston rod sleeve 3.

A coupling element 4 is provided for coupling the actuating element 1 and the piston rod sleeve 3 such that a dose discharging movement of the actuating element 1 can be transmitted to the piston rod 2 via the piston rod sleeve 3 and the coupling sleeve 7. Longitudinally extending ribs 4b are arranged on an inner surface of the coupling element 4 which engage corresponding ribs 3c extending on an outer surface of the piston rod sleeve 3 to provide a rotationally fixed connection between the coupling element 4 and the piston rod sleeve 3. However, due to the rib connection, the coupling element 4 can move axially relative to the piston rod sleeve 3. The coupling element 4 is provided with a flange [SL] 4a with a tooth 4c which can engage with a corresponding coupling element, e.g. a ring of teeth (not shown), arranged on an internal shoulder of the actuating element 1.

A knob 8 is rotatably mounted in the actuating element 1 by means of a snap connection 8a (also referred to as locking cam in the following description). A spring 13 is disposed within the knob 8 and is supported at the distal end on a flange 4a of the coupling element 4 and at the proximal end on a spring holder 14 which is held in the knob 8.

The metering mechanism further comprises a reverse rotation prevention element 5 with a spring arm 5a. The reverse rotation prevention element 5 is rotationally and axially fixed to the housing 6. The spring arm 5a engages a toothing 3b on a radially protruding flange of the piston rod sleeve. The spring arm 5a and the toothing 3b are designed such that the piston rod sleeve 3 can only be rotated in one direction relative to the spring arm 5a, namely during dose discharging.

The coupling sleeve 7, a coupling ring 15, a coupling holder 16 and a clutch spring 17 are mounted in the threaded sleeve 12. At its distal end, the coupling sleeve 7 has an outwardly projecting ring 7c. The coupling ring 15 comprises webs extending in the longitudinal direction which are provided with an annular groove 15a. The ring 7c of the coupling sleeve 7 is axially fixed in the annular groove 15a but free to rotate with respect to the coupling ring 15. A guide cam 15b is arranged at the distal end of the coupling ring 15 for engaging a guide track 16a of the coupling holder 16. The guide track 16a is designed such that the guide cam 15b can be guided with respect to the threaded sleeve 12 during rotation of the coupling ring 15.

The clutch spring 17 is supported at its proximal end on the threaded sleeve 12 and with its distal end on the coupling holder 16. The coupling holder 16 is axially displaceable and rotatable relative to the threaded sleeve 12, whereas the coupling ring 15 is axially movable but rotationally fixed with respect to the threaded sleeve 12. The cartridge holder 18 has a recess 18c which can engage with a cam 16c of the coupling holder 16. The coupling holder 16 has a projection 16b to be guided in the threaded sleeve for attaching the coupling holder 16 with a cartridge holder 18 in a locking position. An inwardly projecting web 15c is mounted on an inner surface of the coupling ring 15 which is received in a longitudinal groove 12c of the threaded sleeve 12. Due to the guide slot between the coupling holder 16 and the coupling ring 15, a rotation of the coupling holder 16 relative to the threaded sleeve 12 results in an axial movement of the coupling ring 15 (with coupling sleeve 7) relative to the threaded sleeve 12, thereby bringing coupling sleeve 7 in an out of engagement with the piston rod sleeve 3 depending on the direction of rotation of the coupling holder, i.e. depending of attachment or detachment of the cartridge holder 18.

In order to set the dose with the injection device of FIG. 1, a user rotates actuating element 1 in a first direction such that the actuating element 1 winds out of housing 6 and housing sleeve 21 guided by external thread 1b. Coupling element 4 is axially entrained by actuating element 1 with flange 4a abutting a respective shoulder in actuating element 1. Tooth 4c rides over the teeth in actuating element 1 compressing spring 13. Due to the splined engagement of the coupling element 4 with the piston rod sleeve 3 the coupling element 4 is prevented from rotation by means of reverse rotation prevention element 5 acting on piston rod sleeve 3. With the cartridge holder 18 attached to the threaded sleeve 12, coupling sleeve 7 and engages piston rod sleeve 3 such that the piston rod 2 is prevented from rotating, too. During dose setting a respective dose value printed on the number sleeve 9 is displayed in the window 21a as of the number sleeve 9 rotates together with actuating element 1.

After a dose has been set, the user may discharge the dose by pushing on knob 8. This compresses spring 13 such that tooth 4c is kept in engagement with the respective teeth of actuating element 1. Further, actuating element 1 is wound back into the housing 6 and housing sleeve 21, wherein rotation of the actuating element 1 is transmitted via the coupling element 4 to the piston rod sleeve 3 and, thus, via coupling sleeve 7 to piston rod 2. Due to the threaded engagement of the piston rod 2 with the threaded sleeve 12, the piston rod 2 translates axially in the distal direction with the flange 11 acting on a bung (not shown) in the cartridge 19.

With the injection device of FIG. 1 an empty cartridge 19 may be replaced with a new cartridge which requires resetting of the piston rod 2 from its distal position back to a retracted proximal position. Replacing the cartridge 19 involves detachment of the cartridge holder 18 from the injection device, in more detail from threaded sleeve insert 12, by rotating the cartridge holder 18 guided with respect to the threaded sleeve insert 12 with locking cam 18a moving within guide 12a. This pure rotational movement is followed by an axial movement of the cartridge holder 18 in the distal direction with respect to the threaded sleeve 12. The rotational movement of the cartridge holder 18 is transmitted to coupling holder 16 which rotates together with the cartridge holder with respect to the threaded sleeve 12, thereby advancing coupling ring 15 in the distal direction such that the coupling sleeve 7 is moved distally, too. This disengages of the coupling sleeve 7 from the piston rod sleeve [sic]3.

Reattachment of the cartridge holder 18 after replacement of the cartridge 19 involves first a proximal movement of the cartridge holder 18 with respect to the threaded sleeve 12 followed by a pure rotational movement. During this rotational movement, coupling ring 15 [sic] is entrained by the cartridge holder 18, thus resulting in proximal displacement of the coupling ring 15 with the coupling sleeve 7 to engage the coupling sleeve 7 with the piston rod sleeve 3.

Figure 2:
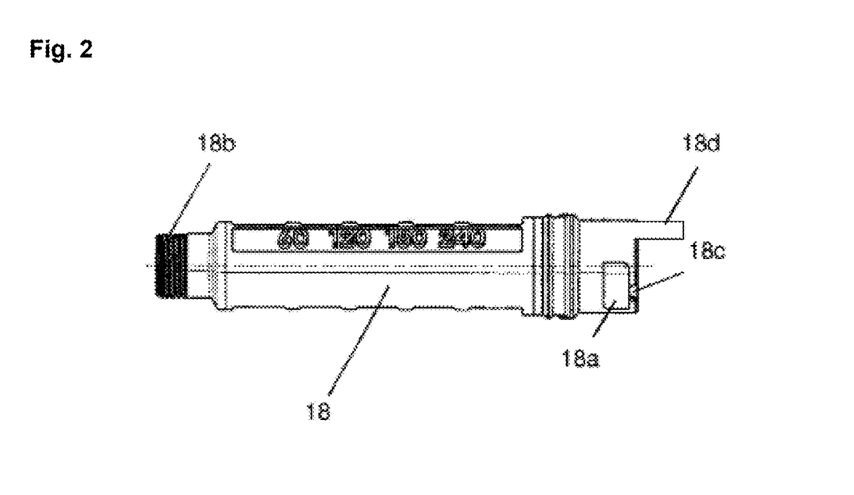
FIG. 2 schematically shows a cartridge holder according to an embodiment of the present disclosure.
Figure 3:
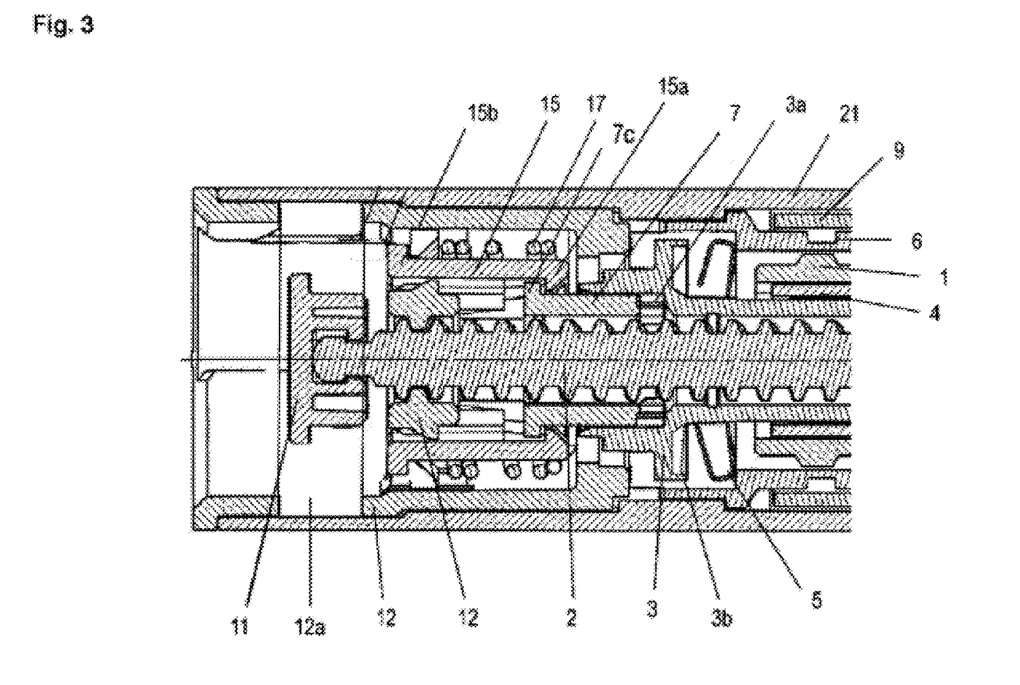
FIG. 3 schematically shows a sectional view of the metering mechanism of an injection device according to an embodiment of the present disclosure.

Turning now to an embodiment of the present disclosure as depicted in FIGS. 2 and 3, the main working principle of dose setting and dose discharging is identical as described above and in EP 2 643 036 B1. The bayonet locking of the cartridge holder 18 with the threaded sleeve insert 12 is substantially the same as described above and in EP 2 643 036 B1, too. The injection device according to the present disclosure may be either a manually driven device as in EP 2 643 036 B1 or a spring driven or spring assisted device.

FIG. 2 shows that the cartridge holder 18 is provided with a protrusion 18d on its proximal side facing towards the threaded sleeve insert 12. FIG. 3 shows that compared to FIG. 1 the coupling holder 16 is [sic] omitted such that the protrusion 18d of the cartridge holder 18 may directly abut the distal face of coupling ring 15 when inserted into the threaded sleeve insert 12 during attachment of the cartridge holder 18. Omitting the coupling holder reduces the number of component parts and simplifies assembly.

In this embodiment, during its axial movement, the cartridge holder 18 pushes with its protrusion 18d on the coupling ring 15, thereby compressing spring 17 and shifting coupling sleeve 7 proximally to engage piston rod sleeve 3. When detaching the cartridge holder 18 from the injection device and the threaded sleeve insert 12 spring 17 pushes the coupling ring 15 together with the coupling sleeve 7 in the distal direction, thereby decoupling of the coupling sleeve 7 from the piston rod sleeve 3.

In the embodiment depicted in FIG. 3, the coupling ring 15 is guided in the threaded sleeve insert 12 such that the coupling ring 15 can be displaced axially with respect to the threaded sleeve insert 12 but is prevented from rotation with respect to threaded sleeve insert 12. The coupling sleeve 7 is axially retained in the coupling ring 15 but free to rotate with respect to coupling ring 15.

As an alternative to the embodiments depicted in FIG. 3, the coupling ring 15 may be omitted in a not shown embodiment, thereby further reducing the number of component parts and further simplifying assembly. In this embodiment, the spring 17 is located interposed between the coupling sleeve 7 and the piston rod sleeve 3, for example between ring 7c and the flange carrying the toothing 3b. In this embodiment the coupling sleeve 7 is guided within the threaded sleeve insert 12 such that the coupling sleeve is free to rotate with respect to threaded sleeve insert 12 and that the limited axial displacement of the coupling sleeve 7 is permitted. The protrusion 18d of the cartridge holder 18 directly abuts the ring 7c of the coupling sleeve 7 when the cartridge holder 18 is inserted into the threaded sleeve insert 12 for attachment. Thus, attachment of the cartridge holder 18 engages of the coupling sleeve 7 with the piston rod sleeve 3, while at detachment of the cartridge holder 18 allows the spring 17 to disengage the coupling sleeve 7 from the piston rod sleeve 3.

In an embodiment of the present disclosure the interface between the cartridge holder 18 and the threaded sleeve insert 12 is the same as in EP 2 643 036 B1, i.e. with the guide 12a having an axially extending portion and a circumferentially extending portion for guiding the locking cam 18a to move axially and to rotate.

As an alternative, the circumferentially extending portion of the guide 12a may be replaced by a helical portion such that the locking cam 18a is guided on a helical path. Preferably, the axial movement of the cartridge holder 18 caused by this helical path results in engaging of the coupling sleeve 7 and with the piston rod sleeve 3 when attaching the cartridge holder 18.

REFERENCE NUMERALS

| 1 | actuating element | 11 | flange |
|---|---|---|---|
| 1a | cam | 12 | threaded sleeve insert |
| 1b | outer thread | 12a | guide |
| 2 | piston rod | 12c | groove |
| 2a | outer thread | 13 | spring |
| 2b | cam | 14 | spring holder |
| 3 | piston rod sleeve | 15 | coupling ring |
| 3a | grooves | 15a | groove |
| 3b | toothing | 15b | cam |
| 3c | ribs | 15c | web |
| 4 | coupling element | 16 | coupling holder |
| 4a | flange | 16a | guide track |
| 4b | ribs | 16b | projection |
| 4c | tooth | 16c | cam |
| 5 | reverse rotation prevention element | 17 | spring |
| 5a | arm | 18 | cartridge holder |
| 6 | housing | 18a | cam |
| 6b | cam | 18b | thread |
| 7 | coupling sleeve | 18c | recess |

-continued

| | | | |
|---|---|---|---|
| 7a | rib | 18d | protrusion |
| 7b | ribs | 19 | catridge |
| 7c | ring | 20 | cap |
| 8 | knob | 21 | housing sleeve |
| 8a | snap feature | 21a | window |
| 9 | number sleeve | | |

The invention claimed is:

1. An injection device, comprising
a housing having a central axis,
a cartridge holder for receiving a cartridge containing a medicament, the cartridge holder having a first attachment member,
a threaded sleeve insert axially and rotationally constrained to the housing, the threaded sleeve insert having a second attachment member, and
a metering mechanism, the metering mechanism comprising
an actuating element for setting or discharging a dose of the medicament from the injection device,
a piston rod for producing an advance movement for dispensing a dose,
a piston rod sleeve for accommodating the piston rod, wherein the piston rod is non-rotatably connected to the piston rod sleeve, and
a coupling element for coupling the actuating element and the piston rod sleeve to discharge the dose with the actuating element in a manner such that a dispensing movement of the actuating element is transmitted to the piston rod by the piston rod sleeve,
wherein the metering mechanism further comprises a reverse rotation prevention element for the piston rod sleeve, to permit rotation of the piston rod sleeve in one direction and to prevent rotation of the piston rod sleeve in an opposite direction,
wherein the piston rod is non-rotatably connected to the piston rod sleeve by a coupling sleeve, wherein the coupling sleeve engages the piston rod sleeve to form a non-rotatable connection between the piston rod and the coupling sleeve, and wherein the piston rod is rotatable relative to the piston rod sleeve when the coupling sleeve is out of engagement with the piston rod sleeve,
wherein the cartridge holder is configured to move axially with respect to the threaded sleeve insert and the housing to attach the cartridge holder to the threaded sleeve insert by an interaction of the first attachment member and the second attachment member and wherein the cartridge holder is configured to bring the coupling sleeve into engagement with the piston rod sleeve by means of said axial movement with respect to the threaded sleeve insert and the housing.

2. The injection device according to claim 1, wherein the cartridge holder comprises at least one axially extending protrusion directly abutting the coupling sleeve while the cartridge holder moves axially to attach to the threaded sleeve insert, such that a common axial movement of the cartridge holder and the coupling sleeve brings the coupling sleeve into engagement with the piston rod sleeve.

3. The injection device according to claim 1, further comprising a coupling ring axially constrained to the coupling sleeve, wherein the cartridge holder comprises a contact face directly abutting the coupling ring while the cartridge holder moves axially to attach to the threaded sleeve insert, such that a common axial movement of the cartridge holder, the coupling ring and the coupling sleeve brings the coupling sleeve into engagement with the piston rod sleeve.

4. The injection device according to claim 3, wherein the coupling ring is axially guided in the threaded sleeve insert and rotatable with respect to the threaded sleeve insert.

5. The injection device according to claim 1, further comprising a clutch spring, wherein the clutch spring exerts a force on the coupling sleeve to bring the coupling sleeve out of engagement with the piston rod sleeve when the cartridge holder is detached from the threaded sleeve insert.

6. The injection device according to claim 5, wherein the clutch spring is interposed between the coupling sleeve and the piston rod sleeve.

7. The injection device according to claim 1, wherein the first attachment member comprises a cam and the second attachment member comprises a guide track, wherein the guide track comprises at least one portion guiding the cartridge holder with the cam axially with respect to the threaded sleeve insert.

8. The injection device according to claim 1, wherein the first attachment member comprises a cam and the second attachment member comprises a guide track, wherein the guide track comprises at least one portion guiding the cartridge holder with the cam on a helical path with respect to the threaded sleeve insert.

9. The injection device according to claim 1, wherein the actuating element is coupled to the coupling element such that an axial movement of the actuating element for setting a dose is transmitted to the coupling element.

10. The injection device according to claim 1, wherein the coupling element comprises a coupling member and the actuating element comprises a counterpart coupling member.

11. The injection device according to claim 10, wherein the coupling member and the counterpart coupling member can be coupled or decoupled relative to each other by an axial displacement of the coupling element relative to the actuating element.

12. The injection device according to claim 10, wherein the coupling member and the counterpart coupling member can be coupled or decoupled relative to each other by a radial displacement of the coupling element relative to the actuating element.

13. The injection device according to claim 10, wherein the actuating element comprises a shoulder as the counterpart coupling member and the coupling element comprises a flange with at least one tooth as the coupling member arranged such that an axial movement of the actuating element for setting a dose is transmitted to the coupling element.

14. The injection device according to claim 10, wherein the coupling member and the counterpart coupling member are each provided with teeth.

15. The injection device according to claim 1, wherein the coupling element comprises grooves and the piston rod sleeve comprises ribs for preventing relative rotation of the coupling element and the piston rod sleeve and permitting relative axial displacement of the coupling element and the piston rod sleeve.

16. The injection device according to claim 1, wherein the reverse rotation prevention element is configured to engage the piston rod sleeve by a tooth or a latch.

17. The injection device according to claim 16, wherein the reverse rotation prevention element comprises a spring arm or is in the form of a spring arm.

18. The injection device according to claim 1, wherein the reverse rotation prevention element and the piston rod sleeve are coupled to each other.

19. The injection device according to claim 1, wherein the reverse rotation prevention element is non-rotatably and axially-fixedly connected to the housing.

20. The injection device according to claim 1, wherein the piston rod is axially displaceable relative to the piston rod sleeve when the coupling sleeve is out of engagement with the piston rod.

21. An injection device, comprising
a housing having a central axis,
a cartridge holder for receiving a cartridge containing a medicament, the cartridge holder having a first attachment member,
a threaded sleeve insert axially and rotationally constrained to the housing, the threaded sleeve insert having a second attachment member, and
a metering mechanism, the metering mechanism comprising
an actuating element for setting or discharging a dose of the medicament from the injection device,
a piston rod for producing an advance movement for dispensing a dose,
a piston rod sleeve for accommodating the piston rod, wherein the piston rod is non-rotatably connected to the piston rod sleeve, and
a coupling element for coupling the actuating element and the piston rod sleeve to discharge the dose with the actuating element in a manner such that a dispensing movement of the actuating element is transmitted to the piston rod by the piston rod sleeve,
wherein the metering mechanism further comprises a reverse rotation prevention element for the piston rod sleeve, to permit rotation of the piston rod sleeve in one direction and to prevent rotation of the piston rod sleeve in an opposite direction,
wherein the piston rod is non-rotatably connected to the piston rod sleeve by a coupling sleeve, wherein the coupling sleeve engages the piston rod sleeve to form a non-rotatable connection between the piston rod and the coupling sleeve, and wherein the piston rod is rotatable relative to the piston rod sleeve when the coupling sleeve is out of engagement with the piston rod sleeve,
wherein the cartridge holder is configured to move axially with respect to the threaded sleeve insert and the housing to attach the cartridge holder to the threaded sleeve insert by an interaction of the first attachment member and the second attachment member to bring the coupling sleeve into engagement with the piston rod sleeve, and
wherein the cartridge holder comprises at least one axially extending protrusion directly abutting the coupling sleeve while the cartridge holder moves axially to attach to the threaded sleeve insert, such that a common axial movement of the cartridge holder and the coupling sleeve brings the coupling sleeve into engagement with the piston rod sleeve.

22. The injection device according to claim 21, wherein the actuating element is coupled to the coupling element such that an axial movement of the actuating element for setting a dose is transmitted to the coupling element.

23. The injection device according to claim 21, further comprising a clutch spring, wherein the clutch spring exerts a force on the coupling sleeve to bring the coupling sleeve out of engagement with the piston rod sleeve when the cartridge holder is detached from the threaded sleeve insert, wherein the clutch spring is interposed between the coupling sleeve and the piston rod sleeve.

24. An injection device, comprising
a housing having a central axis,
a cartridge holder for receiving a cartridge containing a medicament, the cartridge holder having a first attachment member,
a threaded sleeve insert axially and rotationally constrained to the housing, the threaded sleeve insert having a second attachment member, and
a metering mechanism, the metering mechanism comprising
an actuating element for setting or discharging a dose of the medicament from the injection device,
a piston rod for producing an advance movement for dispensing a dose,
a piston rod sleeve for accommodating the piston rod, wherein the piston rod is non-rotatably connected to the piston rod sleeve, and
a coupling element for coupling the actuating element and the piston rod sleeve to discharge the dose with the actuating element in a manner such that a dispensing movement of the actuating element is transmitted to the piston rod by the piston rod sleeve,
wherein the metering mechanism further comprises a reverse rotation prevention element for the piston rod sleeve, to permit rotation of the piston rod sleeve in one direction and to prevent rotation of the piston rod sleeve in an opposite direction,
wherein the piston rod is non-rotatably connected to the piston rod sleeve by a coupling sleeve, wherein the coupling sleeve engages the piston rod sleeve to form a non-rotatable connection between the piston rod and the coupling sleeve, and wherein the piston rod is rotatable relative to the piston rod sleeve when the coupling sleeve is out of engagement with the piston rod sleeve,
wherein the cartridge holder is configured to move axially with respect to the threaded sleeve insert and the housing to attach the cartridge holder to the threaded sleeve insert by an interaction of the first attachment member and the second attachment member to bring the coupling sleeve into engagement with the piston rod sleeve,
the injection device further comprising a coupling ring axially constrained to the coupling sleeve, wherein the cartridge holder comprises a contact face directly abutting the coupling ring while the cartridge holder moves axially to attach to the threaded sleeve insert, such that a common axial movement of the cartridge holder, the coupling ring and the coupling sleeve brings the coupling sleeve into engagement with the piston rod sleeve.

25. The injection device according to claim 24, wherein the coupling ring is axially guided in the threaded sleeve insert and rotatable with respect to the threaded sleeve insert.

26. An injection device, comprising
a housing having a central axis,
a cartridge holder for receiving a cartridge containing a medicament, the cartridge holder having a first attachment member,
a threaded sleeve insert axially and rotationally constrained to the housing, the threaded sleeve insert having a second attachment member, and a metering mechanism, the metering mechanism comprising
- an actuating element for setting or discharging a dose of the medicament from the injection device,
- a piston rod for producing an advance movement for dispensing a dose,
- a piston rod sleeve for accommodating the piston rod, wherein the piston rod is non-rotatably connected to the piston rod sleeve, and
- a coupling element for coupling the actuating element and the piston rod sleeve to discharge the dose with the actuating element in a manner such that a dispensing movement of the actuating element is transmitted to the piston rod by the piston rod sleeve, wherein the metering mechanism further comprises a reverse rotation prevention element for the piston rod sleeve, to permit rotation of the piston rod sleeve in one direction and to prevent rotation of the piston rod sleeve in an opposite direction, wherein the piston rod is non-rotatably connected to the piston rod sleeve by a coupling sleeve, wherein the coupling sleeve engages the piston rod sleeve to form a non-rotatable connection between the piston rod and the coupling sleeve, and wherein the piston rod is rotatable relative to the piston rod sleeve when the coupling sleeve is out of engagement with the piston rod sleeve, wherein the cartridge holder is configured to move axially with respect to the threaded sleeve insert and the housing to attach the cartridge holder to the threaded sleeve insert by an interaction of the first attachment member and the second attachment member to bring the coupling sleeve into engagement with the piston rod sleeve, and wherein the first attachment member comprises a cam and the second attachment member comprises a guide track, wherein the guide track comprises at least one portion guiding the cartridge holder with the cam on a helical path with respect to the threaded sleeve insert.

27. The injection device according to claim 26, wherein the actuating element is coupled to the coupling element such that an axial movement of the actuating element for setting a dose is transmitted to the coupling element.

* * * * *